US008580981B2

(12) United States Patent
Wigerinck et al.

(10) Patent No.: US 8,580,981 B2
(45) Date of Patent: Nov. 12, 2013

(54) PROCESS FOR THE PREPARATION OF (3R,3AS,6AR)-HEXAHYDROFURO [2,3-B] FURAN-3-YL (1S,2R)-3-[[(4-AMINOPHENYL) SULFONYL] (ISOBUTYL) AMINO]-1-BENZYL-2-HYDROXYPROPYLCARBAMATE

(75) Inventors: Piet Tom Bert Paul Wigerinck, Terhagen (BE); Dominique Louis Nestor Ghislain Surleraux, Braine-le-château (BE); Wim Gaston Verschueren, Berchem (BE); Herman Augustinus De Kock, Arendonk (BE); Wim Albert Alex Aelterman, Gierle (BE)

(73) Assignee: Janssen R&D Ireland, Little Island, Co, Cork (IE)

( * ) Notice: Subject to any disclaimer, the term of this patent is extended or adjusted under 35 U.S.C. 154(b) by 230 days.

(21) Appl. No.: 13/060,942

(22) PCT Filed: Sep. 1, 2009

(86) PCT No.: PCT/EP2009/061253
§ 371 (c)(1),
(2), (4) Date: Feb. 25, 2011

(87) PCT Pub. No.: WO2010/023322
PCT Pub. Date: Mar. 4, 2010

(65) Prior Publication Data
US 2011/0160468 A1 Jun. 30, 2011

(30) Foreign Application Priority Data
Sep. 1, 2008 (EP) ..................................... 08163383

(51) Int. Cl.
C07D 493/04 (2006.01)
(52) U.S. Cl.
USPC ....................................................... 549/464
(58) Field of Classification Search
USPC ....................................................... 549/464
See application file for complete search history.

(56) References Cited

U.S. PATENT DOCUMENTS

| 6,248,775 B1 | 6/2001 | Vazquez et al. |
| 6,455,738 B1 | 9/2002 | Dubac et al. |

FOREIGN PATENT DOCUMENTS

| EP | 0715618 B1 | 6/1996 |
| EP | 0754669 B1 | 1/1997 |
| EP | 1029856 B1 | 8/2000 |
| EP | 1067125 B1 | 1/2001 |
| EP | 1081133 B1 | 3/2001 |
| EP | 1215209 B1 | 6/2002 |
| EP | 1466896 A1 | 10/2004 |
| WO | WO 95/06030 A1 | 3/1995 |
| WO | WO 98/07685 A1 | 2/1998 |
| WO | WO 99/48885 A1 | 9/1999 |
| WO | WO 99/67254 A2 | 12/1999 |
| WO | WO 99/67417 A2 | 12/1999 |
| WO | WO 03/022853 A1 | 3/2003 |
| WO | WO 03/106461 A2 | 12/2003 |
| WO | WO 2004/016619 A1 | 2/2004 |
| WO | WO 2005/063770 A1 | 7/2005 |
| WO | WO 2005/087728 A1 | 9/2005 |
| WO | WO 2005/110428 A2 | 11/2005 |
| WO | WO 2007/060249 A1 | 5/2007 |
| WO | WO 2007/060253 A1 | 5/2007 |

OTHER PUBLICATIONS

Alonso, F., et al. "The NiCl$_2$-Li-arene(cat.) Combination: A Versatile Reducing Mixture", Chemical Society Review, vol. 33, pp. 284-293 (2004).
Ghosh, A., et al. "Potent HIV Protease Inhibitors Incorporating High-Affinity P$_2$-Ligands and ®-(Hydroxyethylamino)Sulfonamide Isotere", Bioorganic Medicinal Chemistry Letters, vol. 8, pp. 687-690 (1998).
Ghosh, A., et al. "Darunavir, a conceptually new HIV-1 protease inhibitor for the treatment of drug-resistant HIV", Bioorganic & Medicinal Chemistry, vol. 15, pp. 7576-7580 (2007).
Greene, T. "Protective Groups in Organic Synthesis", John Wiley & Sons, Inc., Cover Page and Table of Contents (1981).
Leggio, A., et al. "Highly Steroselective synthesis of Optically Pure C-Aryl Imines from α-L-Amino Acid Methyl Esters", Synthetic Communications, vol. 33, No. 24, pp. 4331-4338 (2003).
Liley, M., et al. "An Improved Aldehyde Linker for the Solid Phase Synthesis of Hindered Amides", Journal of Organic Chemistry, vol. 71, pp. 1322-1329 (2006).
March, J., Advanced Organic Chemistry, Reactions, Mechanisms, and Structure, Third Edition, pp. 368-369 (1985).
McManus, S., et al. "The Synthesis of Aminoalcohols From Epoxides and Ammonia", Synthetic Communications, vol. 3(3), pp. 177-180 (1973).
Miller, J., et al. "Novel Arylsulfonamides Possessing Sub-Picomolar HIV Protease Activities and Potent anti-HIV Activity Against Wild-Type and Drug-Resistant Viral Strains", Bioorganic & Medicinal Chemistry Letters, vol. 14 pp. 959-963 (2004).
Narasimhan, S., et al. "Novel Enanatiomer-Switching Catalysts for Asymmetric Reductions and Michael Reactions", Tetrahedron Letters, vol. 42, pp. 719-721 (2001).
Shibata, I., et al. "Chemoselective Reductions of Imino Groups by Dibutyltin Chloride Hydride Complex", J. Organic Chemistry, vol. 63, pp. 383-385 (1998).
Surleraux, D., et al. "Discovery and Selection of TMC114, a Next Generation HIV-1 Protease Inhibitor", J. Medicinal Chemistry, vol. 48 pp. 1813-1822 (2005).
International Search Report PCT/EP2009/061253, mailed Nov. 10, 2009.

Primary Examiner — Taofiq A Solola
(74) Attorney, Agent, or Firm — Michael J. Atkins

(57) ABSTRACT

The present invention relates to a process for the preparation of (3R,3aS,6aR)-hexahydrofuro[2,3-b]furan-3-yl(1S,2R)-3-[[(4-aminophenyl)sulfonyl](isobutyl)amino]-1-benzyl-2-hydroxypropylcarbamate as well as novel intermediates for use in said process. (3R,3aS,6aR)-hexahydrofuro[2,3-b]furan-3-yl(1S,2R)-3-[[(4-aminophenyl)sulfonyl](isobutyl)amino]-1-benzyl-2-hydroxypropylcarbamate is particularly useful as an HIV protease inhibitor.

9 Claims, No Drawings

PROCESS FOR THE PREPARATION OF (3R,3AS,6AR)-HEXAHYDROFURO [2,3-B] FURAN-3-YL (1S,2R)-3-[[(4-AMINOPHENYL) SULFONYL] (ISOBUTYL) AMINO]-1-BENZYL-2-HYDROXYPROPYLCARBAMATE

CROSS REFERENCE TO RELATED APPLICATIONS

This application is a national stage application of PCT Application No. PCT/EP2009/061253, filed Sep. 1, 2009, which application claims priority from EP Patent Application No. 08163383.6, filed Sep. 1, 2008, all of which are hereby incorporated by reference in their entirety.

FIELD OF THE INVENTION

The present invention relates to a process for the preparation of (3R,3aS,6aR)-hexahydrofuro[2,3-b]furan-3-yl(1S, 2R)-3-[[(4-aminophenyl)sulfonyl](isobutyl)amino]-1-benzyl-2-hydroxypropylcarbamate as well as novel intermediates for use in said processes, which process is amenable to industrial scaling up.

BACKGROUND

The virus causing the acquired immunodeficiency syndrome (AIDS) is known by different names, including T-lymphocyte virus III (HTLV-III) or lymphadenopathy-associated virus (LAV) or AIDS-related virus (ARV) or human immunodeficiency virus (HIV). Up until now, two distinct families have been identified, i.e. HIV-1 and HIV-2. Hereinafter, HIV will be used to generically denote these viruses.

One of the critical pathways in a retroviral life cycle is the processing of polyprotein precursors by retroviral protease. For instance, during the replication cycle of the HIV virus, gag and gag-pol gene transcription products are translated as proteins, which are subsequently processed by a virally encoded protease to yield viral enzymes and structural proteins of the virus core. Most commonly, the gag precursor proteins are processed into the core proteins and the pol precursor proteins are processed into the viral enzymes, e.g., reverse transcriptase and retroviral protease. Correct processing of the precursor proteins by the retroviral protease is necessary for the assembly of infectious virions, thus making the retroviral protease an attractive target for antiviral therapy. In particular for HIV treatment, the HIV protease is an attractive target.

Several protease inhibitors are on the market or are being developed. Hydroxyethyl-amino sulfonamide HIV protease inhibitors, for example 4-aminobenzene hydroxyethylamino sulfonamides, have been described to have favourable pharmacological and pharmacokinetic properties against wild-type and mutant HIV virus. Amprenavir is a commercially available exponent of this 4-aminobenzene hydroxyethylamino sulfonamide class of protease inhibitors. A process for the synthesis of amprenavir is described in WO99/48885 (Glaxo Group Ltd.).

4-Aminobenzene hydroxyethylamino sulfonamides may also be prepared according to the procedures described in EP 715618, WO 99/67254, WO 99/67417, U.S. Pat. No. 6,248, 775 and WO 2007/060253, and in Bioorganic and Chemistry Letters, Vol. 8, pp. 687-690, 1998, Bioorganic and Medicinal Chemistry Letters 14 (2004)959-963 and J. Med. Chem. 2005, 48, 1813-1822, all of which are incorporated herein by reference.

One protease inhibitor which has been approved in the USA for human clinical use for the treatment of retroviral infections is the compound having the USAN approved name darunavir with the chemical name (3R,3aS,6aR)-hexahydro-furo[2,3-b]furan-3-yl(1S,2R)-3-[[(4-aminophenyl)sulfonyl] (isobutyl)amino]-1-benzyl-2-hydroxypropyl-carbamate and the structure of formula (A):

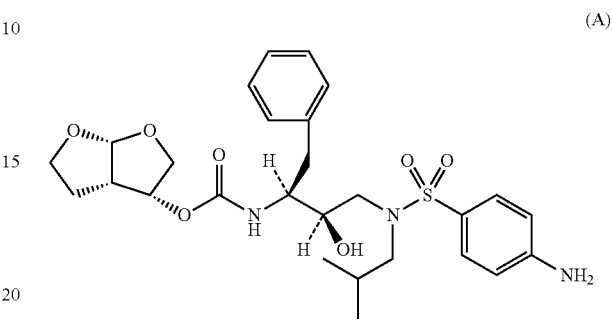

(A)

Darunavir is employed in the clinic in the form of its ethanolate solvate derivative.

Methods suitable for the preparation of darunavir are disclosed in WO 99/67417 (USA, The Secretary, Dpt. of Health and Human Services) and WO 99/67254 (USA, The Secretary, Dpt. of Health and Human Services and The Board of Trustees of the University of Illinois), and in WO 03/106461 (Tibotec N.V.) and WO 2005/063770 (Tibotec Pharmaceuticals).

EP 1466896 (Ajinomoto KK) relates to a process for producing crystalline benzenesulfonamide derivatives. In particular, it provides a crystallization for (2R,3 S)—N-(3-amino-2-hydroxy-4-phenylbutyl)-N-isobutyl-4-amino-benzene-sulfonamide, which is an intermediate of interest for the preparation of darunavir.

In order for a chemical route to be suitable for industrial scale, it should produce compounds in acceptable yields and purity while being easy and simple to carry out, as well as cost-effective. As such, there has been found a new process for the synthesis of darunavir which is amenable for use on an industrial scale.

In particular, the present invention provides a convenient process for the production of darunavir and intermediates, solvates, addition salts, polymorphic and/or pseudopolymorphic forms thereof on an industrial scale.

The reagents further used in said process are safe and available in bulk. Furthermore, each step of said method is performed at controllable conditions and provides the desired compound in optimal yields. Moreover, each step of said process is performed stereoselectively, which allows the synthesis of pure stereoisomeric forms of the desired compounds. The last stage of the process, which involves the reduction of a nitro group to form an amino group, is especially advantageous as it provides the desired compound in a relatively pure form with minimal amounts of associated impurities. Also, many of the stages can be performed sequentially without removal of the intermediate compounds from the reaction vessel.

Other objects and advantages of the present invention will become apparent from the following detailed description taken in conjunction with the accompanying examples.

DETAILED DESCRIPTION OF THE INVENTION

The present invention relates to a process for the preparation of darunavir of formula (A) or a solvate, addition salt or polymorphic or pseudopolymorphic form thereof:

(A)

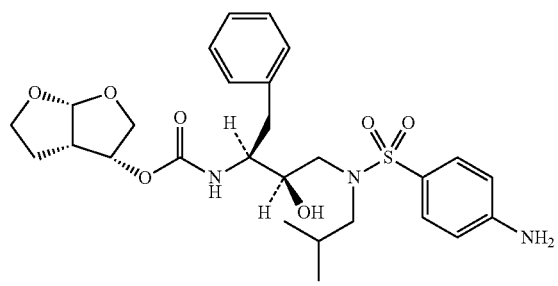

which comprises:

(i) reacting a compound of formula (1):

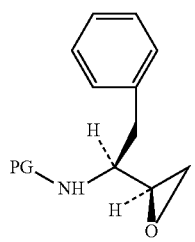

wherein PG represents an amino protecting group, with N-benzyl-isobutylamine, namely a compound of formula (2):

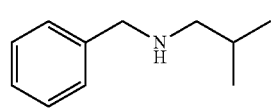

to obtain a compound of formula (3):

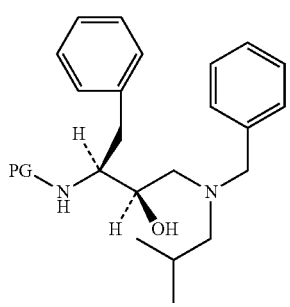

(ii) treating the compound of formula (3) to remove the PG protecting group to obtain a compound of formula (4):

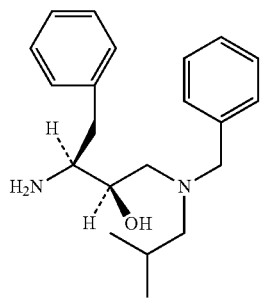

(iii) coupling the compound of formula (4) with a (3R,3aS, 6aR)-hexahydrofuro[2,3-b]furan-3-yl derivative to obtain compound of formula (5):

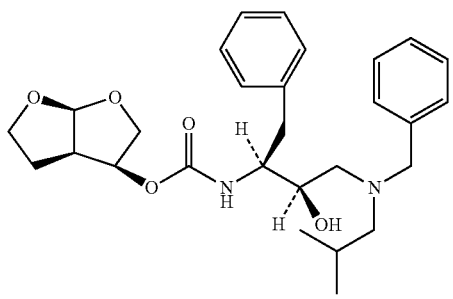

(iv) removing the N-benzyl group from the compound of formula (5) to obtain a compound of formula (6):

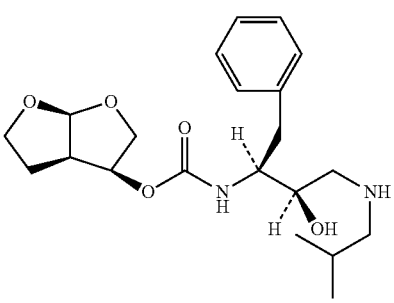

(v) introducing a p-nitrophenylsulfonyl group into the compound of formula (6) to obtain a compound of formula (7):

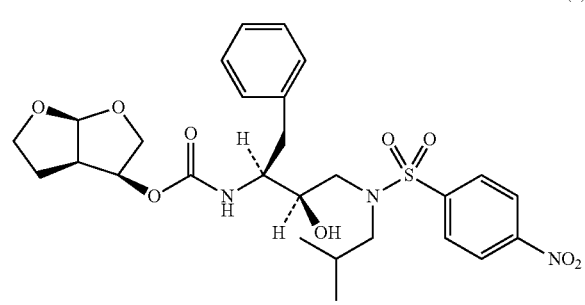

(vi) reducing the nitro group of the compound of formula (7) to form darunavir or a solvate, addition salt or a polymorphic or pseudopolymorphic form thereof.

Compound of Formula (1)

The compound of formula (1) is

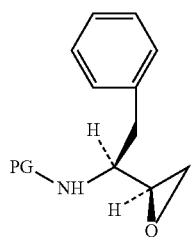

wherein PG represents an amino-protecting group.

The term "amino-protecting group" as used herein refers to one or more selectively removable substituents on the amino group commonly employed to block or protect the amino functionality against undesirable side reactions during synthetic procedures and includes all conventional amino protecting groups. Examples of amino-protecting groups include the urethane blocking groups, such as t-butoxy-carbonyl ("Boc"), 2-(4-biphenylyl)propyl(2)oxycarbonyl ("Bpoc"), 2-phenylpropyl(2)oxycarbonyl ("Poc"), 2-(4-xenyl)isopropoxycarbonyl, isopropoxycarbonyl, 1,1-diphenylethyl(1)-oxycarbonyl, 1,1-diphenylpropyl(1)oxycarbonyl, 2-(3,5-dimethoxyphenyl)propyl(2)-oxycarbonyl ("Ddz"), 2-(p-5-toluoyl)propyl(2)oxycarbonyl, 1-methylcyclopentanyloxycarbonyl, cyclohexanyloxycarbonyl, 1-methylcyclohexanyloxycarbonyl, 2-methylcyclohexanyloxycarbonyl, ethoxycarbonyl, 2-(4-toluoylsulfonyl)ethoxycarbonyl, 2-(methylsulfonyl)-ethoxycarbonyl, 2-(triphenylphosphino)-ethoxycarbonyl, 9-fluoroenyl-methoxycarbonyl ("Fmoc"), 2-(trimethylsilyl)ethoxycarbonyl, allyloxycarbonyl, 1-(trimethylsilylmethyl)prop-1-enyloxycarbonyl, 5-benzisoxalylmethoxy-carbonyl, 4-acetoxybenzyloxycarbonyl, 2,2,2-trichloroethoxycarbonyl, tribromoethoxycarbonyl, 2-ethynyl(2)propoxycarbonyl, cyclopropylmethoxycarbonyl, isobornyloxycarbonyl, 1-piperidyloxycarbonyl, benzyloxycarbonyl ("Z" or "Cbz"), 4-phenylbenzyloxycarbonyl, 2-methylbenzyloxy-carbonyl, α-2,4,5,-tetramethylbenzyloxycarbonyl ("Tmz"), 4-methoxybenzyloxycarbonyl, 4-fluorobenzyloxycarbonyl, 4-chlorobenzyloxycarbonyl, 3-chlorobenzyloxycarbonyl, 2-chlorobenzyloxycarbonyl, dichlorobenzyloxycarbonyl, 4-bromobenzyloxycarbonyl, ortho-bromobenzyloxycarbonyl, 3-bromobenzyloxycarbonyl, 4-nitrobenzyloxycarbonyl, 4-cyanobenzyloxycarbonyl, 4-(decyloxy)benzyloxycarbonyl, and the like; the benzoylmethylsulfonyl group, dithiasuccinoyl ("Dts") group, the 2-(nitro)phenylsulfenyl group ("Nps"), the diphenylphosphine oxide group, and the like. The species of amino-protecting group employed is usually not critical so long as the derivatized amino group is stable to the conditions of the subsequent reactions and can be removed at the appropriate point without disrupting the remainder of the compound.

Additional examples of amino protecting groups include phenylacetyl, formyl ("For"), trityl (Trt), acetyl, trifluoroacetyl (TFA), trichloroacetyl, dichloroacetyl, chloroacetyl, bromoacetyl, iodoacetyl, benzoyl, tert-amyloxycarbonyl, tert-butoxycarbonyl, 3,4-dimethoxybenzyloxycarbonyl, 4-(phenylazo)benzyloxycarbonyl, 2-furfuryloxycarbonyl, diphenylmethoxycarbonyl, 1,1-dimethylpropoxycarbonyl, phthalyl or phthalimido, succinyl, alanyl, leucyl, and 8-quinolyloxycarbonyl, benzyl, diphenylmethyl, 2-nitrophenylthio, 2,4-dinitrophenylthio, methanesulfonyl, paratoluenesulfonyl, N,N-dimethylaminomethylene, benzylidene, 2-hydroxybenzylidene, 2-hydroxy-5-chlorobenzylidene, 2-hydroxy-1-naphthylmethylene, 3-hydroxy-4-pyridylmethylene, cyclohexylidene, 2-ethoxycarbonylcyclohexylidene, 2-ethoxycarbonylcyclopentylidene, 2-acetylcyclohexylidene, 3,3-dimethyl-5-oxycyclohexylidene, diphenylphosphoryl, dibenzylphosphoryl, 5-methyl-2-oxo-2H-1,3-dioxol-4-yl-methyl, trimethylsilyl, triethylsilyl, triphenylsilyl, 2-(p-biphenyl)-1-methylethoxycarbonyl, diisopropylmethoxycarbonyl, cyclopentyloxycarbonyl, adamantyloxycarbonyl, triphenylmethyl, trimethylsilane, phenylthiocarbonyl, paranitrobenzylcarbonyl.

Other amino protecting groups include 2,7-di-t-butyl-[9-(10,10-dioxo-10,10,10,10-tetrahydrothio-xanthyl)]methyloxycarbonyl; 2-trimethylsilylethyloxycarbonyl; 2-phenylethyloxycarbonyl; 1,1-dimethyl-2,2-dibromoethyloxycarbonyl; 1-methyl-1-(4-biphenylyl)ethyloxycarbonyl; p-nitrobenzyloxycarbonyl; 2-(p-toluenesulfonyl)-ethyloxycarbonyl; m-chloro-p-acyloxybenzyloxycarbonyl; 5-benzisoxazolylmethyloxycarbonyl; p-(dihydroxyboryl)benzyloxycarbonyl; m-nitrophenyloxycarbonyl; o-nitrobenzyloxycarbonyl; 3,5-dimethoxybenzyloxycrbonyl; 3,4-dimethoxy-6-nitrobenzyloxycarbonyl; N'-p-toluenesulfonylaminocarbonyl; t-amyloxycarbonyl; p-decyloxybenzyloxycarbonyl; 2,2-dimethoxycarbonylvinyloxycarbonyl; di(2-pyridyl)methyloxycarbonyl; 2-furanylmethyloxycarbonyl; dithiasuccinimide; 2,5-dimethylpyrrole; 5-dibenzylsuberyl; and, methanesulfonamide. The preferred amino-protecting group is Boc.

Other protecting groups include benzyl; diphenylmethyl (i.e. benzhydryl); trityl (triphenylmethyl); alpha methyl-benzyl; 4-methoxybenzyl; (4,4'-methoxydiphenyl)-methyl; 2,4-dimethoxybenzyl; 2-hydroxybenzyl; or 4-nitrobenzyl; 2-nitrobenzyl; such groups may be removed by hydrogenation with Pd/C/ethanol or with ammonium formamide/Pd/C/ethanol/acetic acid; an alternative protecting group is 2,4-dinitrobenzyl which may be removed with a base such as ammonia, piperidine, morpholine, and a polar solvent such as dimethylformamide or acetonitrile.

Further examples of amino-protecting groups are well known in organic synthesis and the peptide art and are described by, for example T. W. Greene and P. G. M. Wuts, Protective Groups in Organic Synthesis, 2nd ed., John Wiley and Sons, New York, Chapter 7, 1991; M. Bodanzsky, Principles of Peptide Synthesis, 1st and 2nd revised ed., Springer- Verlag, New York, 1984 and 1993; Stewart and Young, Solid Phase Peptide Synthesis, 2nd ed., Pierce Chemical Co, Rockford, Ill. 1984; L. Fieser and M. Fieser, Fieser and Fieser's Reagents for Organic Synthesis, John Wiley and Sons (1994); L. Paquette, ed. Encyclopedia of Reagents for Organic Synthesis, John Wiley and Sons (1995). Suitable amino protecting groups are also given in e.g. WO98/07685.

Preferably compound of formula (1) is compound of formula (1') as shown below wherein PG is a tert-butyloxycarbonyl or "Boc" group. Compounds of formula (1) and (1') are commercially available and may be prepared in several ways available in the literature, for example as described in WO95/06030 (Searle & Co.), as described by Kaneka Corporation in EP0754669 EP1029856 and EP1067125, and as disclosed by Ajinomoto KK in EP1081133 and EP1215209.

(1')

The compound of formula (1) is subjected to an amination on the epoxide with the compound of formula (2) to obtain the compound of formula (3):

(1)   (3)

The term "amination" as used herein refers to a process in which an amine, namely N-benzyl-isobutylamine of formula (2), is introduced into the organic molecule of formula (1) Amination of compound of formula (1) may be accomplished in conventional manner for example as described below.

In a preferred embodiment, the compound of formula (1') is reacted with N-benzyl-isobutylamine of formula (2) to yield a compound of formula (3'):

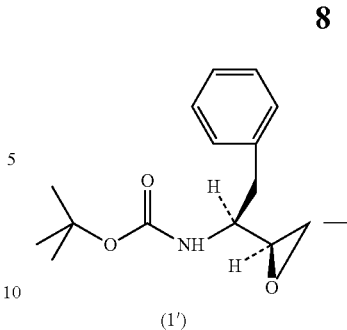

(1')

(3')

The compound of formula (3') is a novel compound and constitutes a further feature of the present invention.

The present invention therefore provides the compound of formula (3'):

(3')

including other stereoisomeric forms, and addition salts and solvates (including hydrates) thereof. In particular, the invention provides for the compound of formula (3') for the preparation of a HIV protease inhibitor, more in particular, for the preparation of darunavir or a solvate, addition salt or polymorphic or pseudopolymorphic form thereof.

Amination of epoxides is described for instance in March, Advanced Organic Chemistry 368-69 (3rd Ed. 1985) and McManus et al., 3 Synth. Comm. 177 (1973), which are incorporated herein by reference.

The amination process is generally performed in the presence of one or more solvents. Suitable solvents include protic, non-protic and dipolar aprotic organic solvents such as, for example, those wherein the solvent is an alcohol, such as methanol, ethanol, isopropanol, n-butanol, t-butanol, and the like; ketones such as acetone; ethers such as diethyl ether, tetrahydrofuran, dioxane and the like; esters such as ethyl acetate; amines such as triethylamine; amides such as N,N-dimethylformamide, or dimethylacetamide; chlorinated solvents such as dichloromethane and other solvents such as toluene, dimethyl sulfoxide, acetonitrile, and mixtures thereof. A preferred solvent is toluene.

Conveniently the reaction can be conducted over a wide range of temperatures, e.g. from about −20° C. to about 200° C., but is preferably, although not necessarily, conducted at a temperature at which the solvent refluxes, i.e. between 40° C. and 100° C., more preferably between 60° C. and 90° C.

In an embodiment of the invention, the amination reaction is carried out with N-benzyl-isobutylamine, using isopropyl alcohol as solvent, and heating at about 82° C. for about three hours.

N-Benzyl-isobutylamine used in the above process may be prepared in conventional manner for example by reacting benzaldehyde with isobutylamine to form an imine of formula (2') which is then reduced to form the desired compound of formula (2):

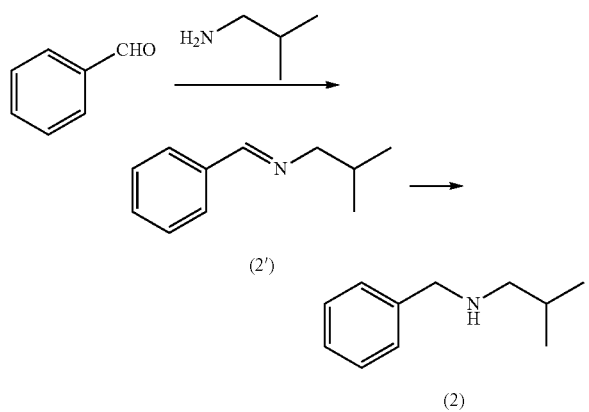

The reaction of the benzaldehyde and isobutylamine can be effected under various conditions, for example by the following procedures:
(a1) with sodium sulphate, magnesium sulphate or triethylamine in a solvent such as methanol, ethanol, tetrahydrofuran, diethyl ether, toluene, benzene, dichloromethane or a solvent mixture such as methanol/dichloromethane, benzene/ethanol at a temperature between room temperature and reflux temperature;
(a2) with sodium hydroxide, potassium hydroxide or lithium hydroxide in a solvent such as ethanol, methanol, isopropanol, water or a solvent mixture such as ethanol/water at a temperature between room temperature and reflux temperature;
(a3) with potassium carbonate or sodium carbonate in methanol at a temperature between room temperature and reflux temperature;
(a4) with a molecular sieve in dichloromethane at room temperature, with the amine present as the ammonium chloride salt. (Synthetic Communications, 33:24, 4331-4338);
(a5) with titanium chloride, triethylamine and sodium sulphate anhydride in dichloromethane at room temperature, with the amine present as the ammonium chloride salt. (Synthetic Communications, 33:24, 4331-4338);
(a6) with sodium methanolate or lithium methanolate in methanol at a temperature between room temperature and 55-60° C.;
(a7) with sodium acetate in methanol or ethanol at a temperature between room temperature and reflux temperature;
(a8) with methyl orthoformate as solvent and to remove the water;
(a9) with p-toluene-sulphonic acid in toluene or xylene, water being removed by azeotropic distillation;
(a10) with toluene or xylene as solvent, water being removed by azeotropic distillation;
(a11) with methanol, ethanol or dichloromethane as solvent at a temperature between room temperature and reflux temperature;
(a12) with solvent mixtures comprising water/ethanol, water/methanol, methanol/dichloromethane or ethanol/dichloromethane at a temperature between room temperature and reflux temperature; or
(a13) with sodium in a methanol solvent.

The reaction of the benzaldehyde and isobutylamine is most preferably effected for example in an appropriate organic solvent such as methanol, generally at a slightly elevated temperature for example 20-50° C. preferably in the range 18-36° C.

The resulting imine compound of formula (2') can then be reduced to form a compound of formula (2) using various reduction procedures for example:
(b1) with sodium borohydride (if desired in combination with zirconium tetrachloride, cerium chloride, titanium tetrachloride, nickel chloride, palladium chloride or tetra isopropoxy titanium), lithium borohydride, potassium borohydride, lithium aluminium borohydride, zinc borohydride, alkyl borohydrides, sodium borohydride acetate, sodium borohydride triacetate, sodium cyano borohydride, lithium cyano borohydride or borane in a solvent such as methanol, ethanol, isopropanol, tetrahydrofuran, diethyl ether or aqueous acetonitrile, for example in the presence of an acid such as acetic acid, trifluoracetic acid or hydrochloric acid;
(b2) with hydrogen and a catalyst comprising Pd/C, RaNi, Pt/C or $PtO_2$ in a solvent comprising methanol, ethanol, isopropanol or tetrahydrofuran;
(b3) with zinc in an acid medium; or $zinc/CeCl_3$ or $CeCl_3.7H_2O$, in a solvent comprising tetrahydrofuran;
(b4) with formic acid;
(b5) with a N-dibutyltin chloride hydride-hexamethylphosphoramide (HMPA) complex in a solvent comprising tetrahydrofuran (JOC 1998, 63, 383-385);
(b6) with sodium in ethanol;
(b7) sodium cyanoborohydride and acetic acid in N,N-dimethylformamide (JOC 2006, 71 (4), 1322-1329);
(b8) with n-tetrabutylammonium borohydride in a solvent comprising tetrahydrofuran or dichloromethane at room temperature (Tetrahedron Letters 42 (2001) 719-721);
(b9) with rhodium, iridium or ruthenium-chiral phosphines (example BINAP=2,2-Bis(diphenylphosphino)-1,1'-binaphthyl) complexes and hydrogenation in a solvent comprising methanol or benzene;
(b10) with Red-Al (bis(2-methoxy ethoxy)aluminiumhydride) or DIBAL (diisobutyl aluminium hydride) in a benzene solvent at room temperature;
(b11) with an amine-borane and acetic acid in a dichloromethane solvent;
(b12) with sodium cyanoborohydride and zinc chloride in solvent mixture comprising diethyl ether/methanol;
(b13) with triethylsilylhydride or dimethylphenylsilylhydride in the presence of trifluoracetic acid; or
(b14) with a nickel chloride-lithium—(for example polymer supported) arene catalyst in the presence of naphthalene or DTBB (4,4'-bis(1,1-dimethylethyl)-1,1'-biphenyl) as electron carrier (Chemical Society Reviews. 2004, 33, 284-293).

The resulting imine compound of formula (2') is most preferably reduced for example by treatment with sodium borohydride, conveniently in an organic solvent such as methanol at a low temperature for example 0-5° C.

The compound of formula (4) is obtained by deprotecting a compound of formula (3) under conventional acidic conditions. Alternatively basic conditions may be applied.

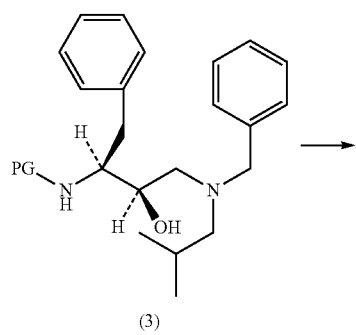

(3)

In a preferred embodiment a compound of formula (4) may be prepared by deprotecting a compound of formula (3')

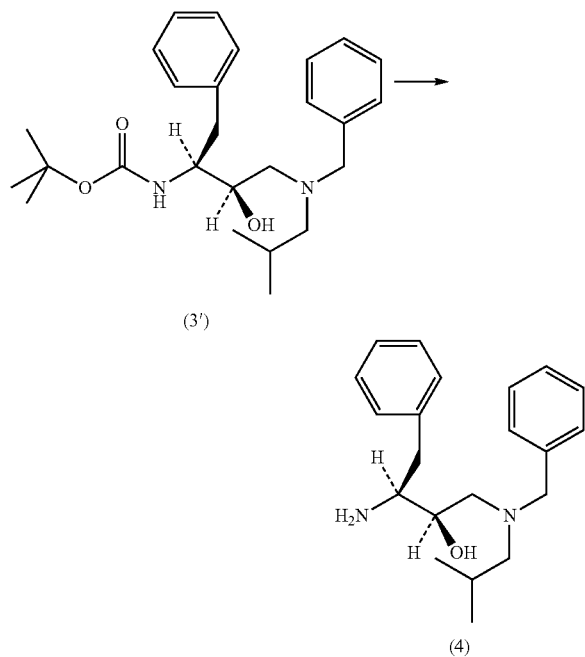

The compound of formula (4) is a novel compound and constitutes a further embodiment of the present invention.

The present invention therefore provides the compound of formula (4):

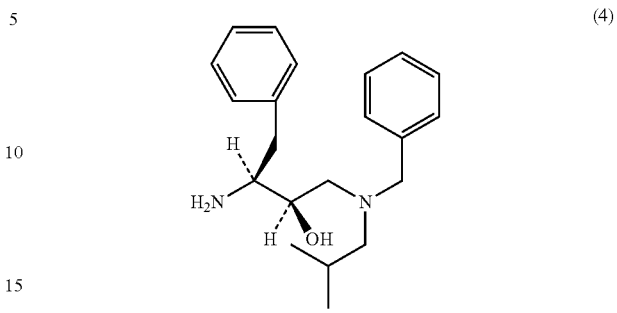

including other stereoisomeric forms, and addition salts and solvates (including hydrates) thereof. In particular, the invention provides for the compound of formula (4) for the preparation of a HIV protease inhibitor, more in particular, for the preparation of darunavir or a solvate, addition salt or polymorphic or pseudopolymorphic form thereof.

Removal of the amino-protecting-group can be achieved using conditions which will not affect the remaining portion of the molecule. These methods are well known in the art and include acid hydrolysis, hydrogenolysis and the like, thus using commonly known acids in suitable solvents.

Examples of acids employed in the removal of the amino protecting group include inorganic acids such as hydrogen chloride, nitric acid, hydrochloric acid, sulfuric acid and phosphoric acid; organic acids such as acetic acid, trifluoroacetic acid methanesulfonic acid and p-toluenesulfonic acid; Lewis acids such as boron trifluoride; acidic cationic ion-exchange resins such as Dowex 50W™. Of these acids, inorganic acids and organic acids are preferred. Hydrochloric acid, sulfuric acid, phosphoric acid and trifluoroacetic acid are more preferred, and hydrochloric acid is most preferred.

The solvent employed during the deprotection of intermediates of formula (3) and (3') is not particularly limited provided that it has no adverse effect on the reaction and dissolves the starting materials to at least some extent. Suitable solvents are aliphatic hydrocarbons such as hexane, heptane and petroleum ether; aromatic hydrocarbons such as benzene, toluene, xylene and mesitylene; halogenated hydrocarbons such as methylene chloride, chloroform, carbon tetrachloride and dichloroethane; ethers such as diethyl ether, tetrahydrofuran, 1,4-dioxane and 1,2-dimethoxyethane; alcohols such as methanol, ethanol, propanol, isopropanol and butanol; esters such as methyl acetate, ethyl acetate, methyl propionate and ethyl propionate; nitrites such as acetonitrile; amides such as N,N-dimethylformamide and N,N-dimethylacetamide; sulfoxides such as dimethyl sulfoxide and mixtures thereof. Aromatic hydrocarbons, alcohols and esters are preferred. Alcohols and water are more preferred, and water, isopropanol, ethanol and methanol are particularly preferred, ethanol being most preferred as a solvent.

The reaction temperature employed depends upon various factors such as the nature of the starting materials, solvents and acids. However it is usually between −20° C. and 150° C., and is preferably between 30° C. and 100° C., even more preferably at a temperature of reflux.

Examples of reagents and methods for deprotecting amines from amino protecting groups can additionally be found in *Protective Groups in Organic Synthesis* by Theodora W. Greene, New York, John Wiley and Sons, Inc., 1981, incorporated herein by reference.

As those skilled in the art will recognize, the choice of amino protecting group employed in a previous step of the process will dictate the reagents and procedures used in removing said amino protecting group.

The compound of formula (5) is obtained by coupling a compound of formula (4) with a (3R,3aS,6aR)-hexahydrofuro[2,3-b]furan-3-yl derivative:

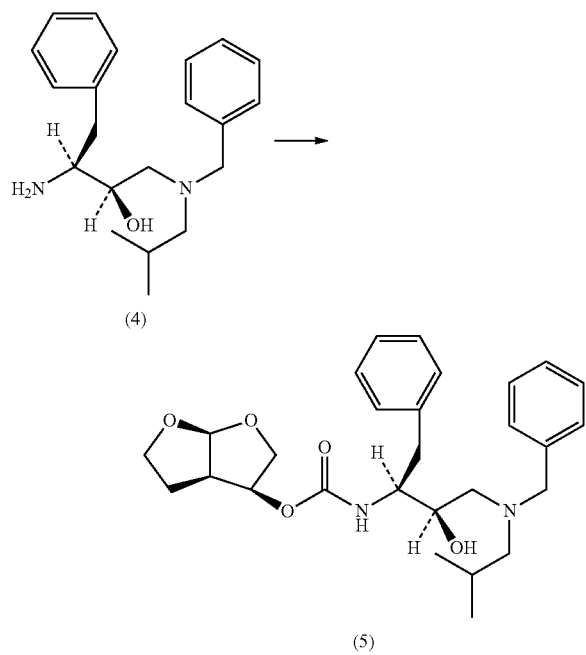

The compound of formula (5) is a novel compound and therefore constitutes a further embodiment of the present invention.

The present invention therefore provides the compound of formula (5):

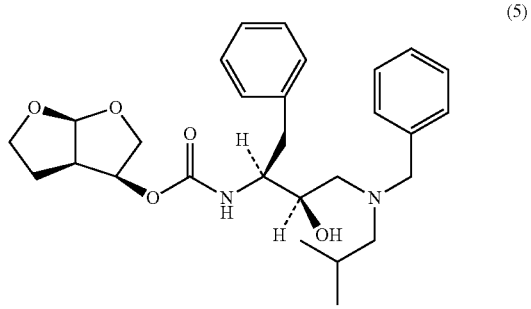 [SMILES: CC(C)CN(Cc1ccccc1)C[C@@H](O)[C@H](Cc1ccccc1)NC(=O)O[C@@H]1CO[C@@H]2OCC[C@@H]21]

including other stereoisomeric forms, and addition salts and solvates (including hydrates) thereof. In particular, the invention provides for the compound of formula (5) for the preparation of a HIV protease inhibitor, more in particular, for the preparation of darunavir or a solvate, addition salt or polymorphic or pseudopolymorphic form thereof.

The (3R,3aS,6aR)-hexahydrofuro[2,3-b]furan-3-yl derivative employed in the above reaction comprising (3R, 3aS,6aR)-hexahydrofuro[2,3-b]furan-3-ol and precursors thereof, may be synthesised as described in WO 03/022853. (3R,3aS,6aR)-hexahydrofuro[2,3-b]furan-3-ol and precursors thereof are suitably activated with coupling agents to generate a (3R,3aS,6aR)-hexahydrofuro[2,3-b]furan-3-yl derivative which may undergo carbamoylation with compound of formula (4). Activation of (3R,3aS,6aR)-hexahydrofuro[2,3-b]furan-3-ol and precursors thereof with the coupling agent preferably occurs before the coupling with compound of formula (4). Said activation of (3R,3aS,6aR)-hexahydrofuro[2,3-b]furan-3-ol and precursors thereof and their coupling to compound of formula (4) has the additional advantage of being a one-pot procedure, since isolation of the activated intermediate is not necessary.

Precursors of (3R,3aS,6aR)-hexahydrofuro[2,3-b]furan-3-ol are those compounds where the oxygen of the alcohol function is protected with O-protecting groups, such as t-butyl ether ("Boc"), acetates, benzyl groups, benzyl ethers, allyls, silyl protecting groups such as tert-butyldimethylsilyl (TBS), trimethylsilylethoxymethyl (SEM), alkoxyalkyl groups such as methoxyethoxymethyl (MEM), methoxymethyl (MOM), tetrahydropyranyl (THP), tetrahydropyranyl (THE), and the like. Where precursors of (3R,3aS,6aR)-hexahydrofuro[2,3-b]furan-3-ol are employed, deprotection may be accomplished prior to the coupling or in situ. Removal of the alcohol protecting groups may be achieved in acidic or basic conditions, being acidic conditions preferred. Protecting groups are well known in the art, see for example Greene, T. W. Protective Groups in Organic Synthesis, John Wiley and Sons, Inc. New York, 1991.

Alternatively, (3R,3aS,6aR)-hexahydrofuro[2,3-b]furan-3-ol and precursors thereof may be obtained through a dynamic diastereoselective resolution of a racemate mixture of hexahydrofuro[2,3-b]furan-3-ol. In such a case, the racemate mixture is submitted to the action of certain enzymes such as porcine pancreatic lipase, candida cylindracea, pancreatin, and the like, in the presence of suitable solvents and reagents such as acetic anhydride, and vinyl acetate. This alternative route allows the in situ production of the desired (3R,3aS,6aR)-hexahydrofuro[2,3-b]furan-3-ol enantiomer, which can be conveniently activated in a one-pot procedure; the undesired stereoisomer is blocked or rendered inert.

Examples of coupling agents used in carbamoylation reactions are carbonates such as bis-(4-nitrophenyl)carbonate, disuccinimidyl carbonate (DSC), carbonyl diimidazole (CDI). Other coupling agents include chloroformates, such as p-nitrophenylchloroformate, phosgenes such as phosgene and triphosgene.

In particular, when the (3R,3aS,6aR)-hexahydrofuro[2,3-b]furan-3-ol is processed with disuccinimidyl carbonate, 1-([[(3R,3aS,6aR)hexahydrofuro[2,3-b]furan-3-yloxy]-carbonyl]oxy)-2,5-pyrrolidinedione is obtained. Said compound is a preferred (3R,3aS,6aR)-hexahydrofuro[2,3-b]furan-3-yl derivative.

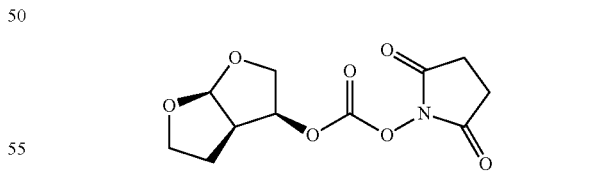

The reaction of (3R,3aS,6aR)-hexahydrofuro[2,3-b]furan-3-ol with disuccinimidyl carbonate may be effected for example by dissolution of the furan-3-ol compound in a suitable solvent such as acetonitrile and addition of a base such as triethylamine followed by addition of the disuccinimidyl carbonate, maintaining the temperature preferably below 35° C. The reaction mixture is preferably stirred at a temperature of about 20° C. for a period of about three hours.

Reaction of a (3R,3aS,6aR)-hexahydrofuro[2,3-b]furan-3-yl derivative with the compound of formula (4) will be performed in the presence of a suitable solvents such as tetrahydrofuran, dimethylformamide, acetonitrile, dioxane, dichloromethane or chloroform, and optionally with bases, such as triethylamine although further combinations from the solvents and bases hereinabove disclosed are also embodied.

Among the solvents, preferred solvents are aprotic solvents such as tetrahydrofuran, acetonitrile, dimethylformamide, ethyl acetate, and the like, dimethylformamide being especially preferred. The reaction is preferably carried out in the presence of a base such as triethylamine to achieve a pH of preferably 7-8.

The carbamoylation reaction is suitably carried out at a temperature between −70° C. and 40° C., preferably between −10° C. and 20° C., especially 15-18° C.

The compound of formula (6) may be obtained by removing the N-benzyl group from a compound of formula (5):

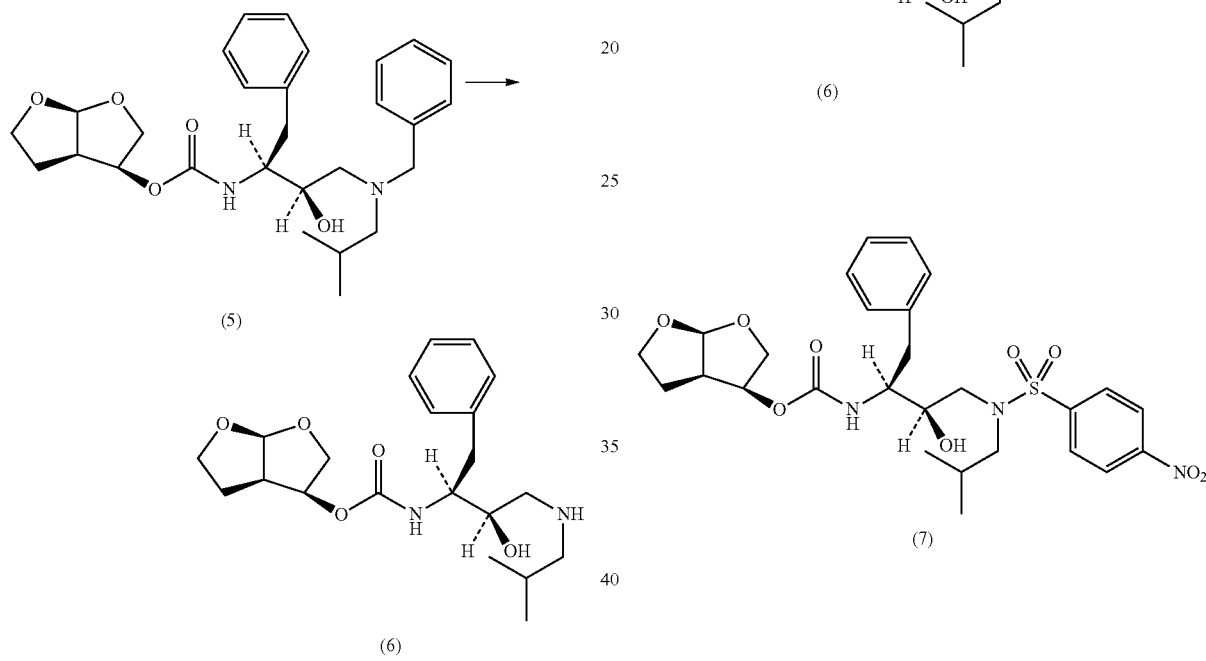

(5)

(6)

The compound of formula (6) is disclosed in patent specifications WO 2004/016619, WO 2005/110428, 2005/087728, WO 2007/060249 and WO 2007/060253.

The removal of the N-benzyl protecting group may be effected in conventional manner for example by any of the following procedures:
(c1) with hydrogen in the presence of a Pd/C or Pd(OH)$_2$ catalyst, optionally in the presence of an acid such as formic acid, acetic acid or hydrochloric acid, optionally in the presence of a base such as potassium carbonate or hydrazine hydrate, optionally in the presence of sodium hypophosphate or ammonium formamide, in a solvent comprising methanol, ethanol, tetrahydrofuran, cyclohexene or cyclohexadiene, at room temperature or an elevated temperature, and optionally under atmospheric or super-atmospheric pressure;
(c2) with sodium and ammonia;
(c3) with lithium and a base such as ethylamine, bismethylamine or triethylamine, in a solvent such as tert-butanol or tetrahydrofuran; or
(c4) with polymethylhydrosiloxane, Pd(OH)$_2$, and an ethanol solvent, at room temperature.

The removal of the N-benzyl protecting group is most preferably effected in by catalytic reduction with Pd/C in an appropriate organic solvent such as methanol, at an elevated temperature, preferably 20-50° C.

The compound of formula (7) is prepared by introducing the sulfonyl moiety, p-nitrobenzene-SO$_2$—, into the intermediate of formula (6):

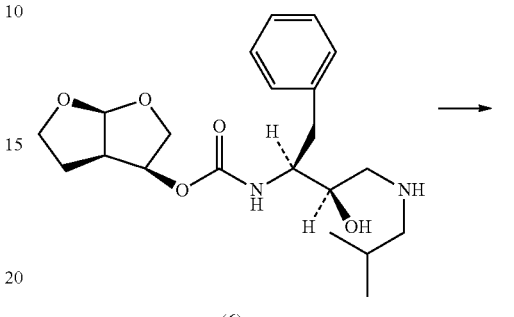

(6)

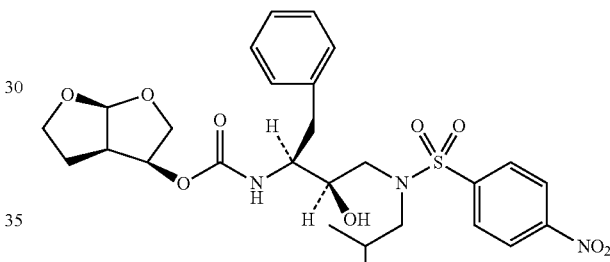

(7)

The compound of formula (7) is disclosed in J. Med. Chem. 2005, 48, 1813-1822.

The compound of formula (6) may therefore be reacted with a sulfonylating agent to obtain a compound of formula (7).

The term "sulfonylation" as used herein refers to a process in which p-nitrobenzene-sulfonyl moeity is introduced into the organic molecule of formula (6). The term "sulfonation" as used herein refers to a process in which a sulfonylating agent is prepared. The term "sulfonylating agent" refers to p-nitrobenzene-sulfonyl derivatives, such as p-nitrobenzene-sulfonyl halo derivatives; the term "halo" as used herein is generic to fluoro, chloro, bromo and iodo.

The sulfonylating agents, and in particular p-nitrobenzenesulfonyl halo derivatives, can be prepared by the oxidation of thiols to sulfonyl chlorides using chlorine in the presence of water under carefully controlled conditions. Additionally, sulfonic acids may be converted to sulfonyl halides using reagents such as PCl$_5$, and also to anhydrides using suitable dehydrating reagents. The sulfonic acids may in turn be prepared using procedures well known in the art. Such sulfonic acids are also commercially available. Sulfonylating agents may as well be prepared by the sulfonation procedures described in "Sulfonation and Related Reactions", by E. E.

Gilbert, R. E. Krieger Publishing Co. Huntington, N.Y. (1977), "Mechanistic Aspects of Aromatic Sulfonation and Desulfonation", by H. Cerfontain, Interscience Publishers, New York (1968), and in U.S. Pat. No. 6,455,738, "Process for the sulfonation of an aromatic compound", all incorporated herein by reference.

The treatment of compounds of formula (6) with the sulfonylating agent can be carried out in the presence of a solvent keeping the temperature preferably at 0-5° C. during the initial reaction, and then maintaining the temperature preferably at about 20° C. After the sulfonylation, any remaining sulfonylating agent or salts are preferably, although not necessarily, removed from the reaction mixture. This removal can be accomplished by repeated washing with water, change of pH, separation of organic and aqueous phases, ultrafiltration, reverse osmosis, centrifugation, and/or filtration or the like.

The compound of formula (7) may be prepared by reacting a sulfonylating agent with the compound of formula (6) in a suitable solvent under alkaline conditions. Suitable alkaline conditions include conventional non-nucleophilic inorganic or organic bases and/or acid scavengers. Conventional non-nucleophilic inorganic or organic bases include, for example, hydrides, hydroxides, amides, alcoholates, acetates, carbonates, or hydrogen carbonates of alkaline earth metals or alkali metal hydrides such as, for example, sodium hydride, potassium hydride or calcium hydride, and metal amides, such as sodium amide, potassium amide, lithium diisopropylamide or potassium hexamethyldisilazide, and metal alkanes such as sodium methylate, sodium ethylate, potassium tert-butylate, sodium hydroxide, potassium hydroxide, ammonium hydroxide, sodium acetate, potassium acetate, calcium acetate, ammonium acetate, sodium carbonate, sodium bicarbonate, potassium carbonate, potassium bicarbonate, cesium carbonate, potassium hydrogen carbonate, sodium hydrogen carbonate, or ammonium carbonate, and also basic organic nitrogen compounds such as, trialkylamines, like trimethylamine, triethylamine, tributylamine, N,N-dimethylaniline, N,N-dimethyl-benzylamine, N,N-diisopropylethylamine, pyridine, 1,4-diazabicyclo-[2.2.2]-octane (DABCO), 1,5-diazabicyclo[4.3.0]-non-5-ene (DBN), or 1,8-diazabicyclo[5.4.0]-undec-7-ene (DBU), or an excess of an appropriate piperidine compound may be used. Preferably triethylamine is used.

Suitable solvents for use in the sulfonylation of the compound of formula (6) above, include for example toluene, ethyl acetate, methylene chloride, dichloromethane, and tetrahydrofuran, chloroform being especially preferred.

The desired compound darunavir is obtained by reducing the nitro moiety of the compound of formula (7) with a reducing agent, optionally under a hydrogen atmosphere.

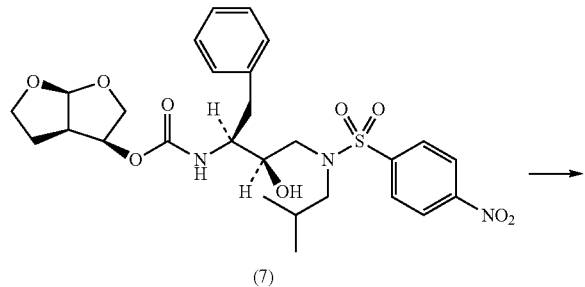

(7)

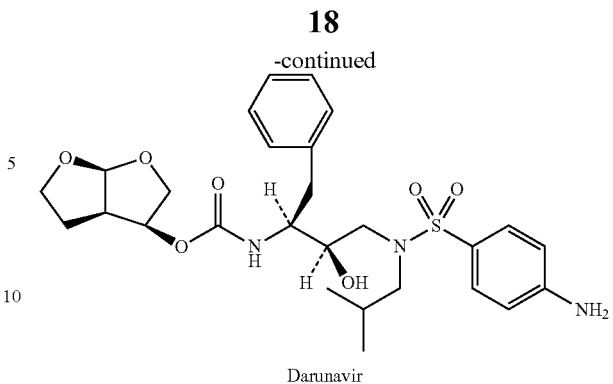

Darunavir

Reducing agents suitable for reduction of the nitro moiety are metallic reducing reagents such as borane complexes, diborane, sodium borohydride, lithium borohydride, sodium borohydride-LiCl, aluminum lithium hydride, or diisobutyl-aluminium hydride; metals such as iron, zinc, tin and the like; and transition metals such as palladium-carbon, platinum oxide, Raney-nickel, rhodium, ruthenium and the like. When catalytic reduction is applied, ammonium formate, sodium dihydrogen-phosphate, hydrazine may be used as the hydrogen source.

Solvents suitable for the reduction of the nitro moiety may be selected from water, alcohols, such as methanol, ethanol, isopropanol, tert-butyl alcohol, esters such as ethyl acetate, amides such as dimethylformamide, acetic acid, dichloromethane, toluene, xylene, benzene, pentane, hexane, heptane, petrol ether, 1,4-thioxane, diethyl ether, diisopropyl ether, tetrahydrofuran, 1,4-dioxane, 1,2-dimethoxiethane, dimethyl sulfoxide, or mixtures thereof. In general any solvent susceptible to being used in a chemical reduction process may be used.

The reduction step can be carried out at temperatures between 0° and 100° C., the preferred temperatures lying between 10° C. and 70° C., more preferably between 20° C. and 60° C. The reaction time may range from 30 minutes to 2 days, more suitably from 1 hour up to 24 hours. According to a preferred embodiment, the reduction step is performed using palladium on charcoal suspended in ethyl acetate.

In each of the preparations presented above, the reaction products, for instance compounds of formula (3), (3'), (4), (5), (6), (7) and the end product darunavir may be isolated from the reaction medium and, if necessary, further purified according to methodologies generally known in the art such as, for example, extraction, crystallization, distillation, trituration and chromatography.

For therapeutic use, the salts of darunavir, are those wherein the counter-ion is pharmaceutically or physiologically acceptable. However, salts having a pharmaceutically unacceptable counterion may also find use, for example, in the preparation or purification of a pharmaceutically acceptable compound of the present invention. All salts, whether pharmaceutically acceptable or not are included within the ambit of the present invention.

The pharmaceutically acceptable salts of darunavir, i.e. in the form of water-, oil-soluble, or dispersible products, include the conventional non-toxic salts or the quaternary ammonium salts which are formed, e.g., from inorganic or organic acids or bases. Examples of such acid addition salts include acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, phosphate, pamoate, pectinate, persulfate, 3-phenylpropionate, picrate, pivalate, propionate, succinate, tartrate, thiocyanate, tosylate, and undecanoate. Base salts include ammonium salts, alkali metal salts such as sodium and potassium salts, alkaline earth metal salts such as calcium and magnesium salts, salts with organic bases such as dicyclohexylamine salts, N-methyl-D-glucamine, and salts with amino acids such a sarginine, lysine, and so forth. Also, the basic nitrogen-containing groups may be quaternized with such agents as lower alkyl halides, such as methyl, ethyl, propyl, and butyl chloride, bromides and iodides; dialkyl sulfates like dimethyl, diethyl, dibutyl; and diamyl sulfates, long chain halides such as decyl, lauryl, myristyl and stearyl chlorides, bromides and iodides, aralkyl halides like benzyl and phenethyl-bromides and others. Other pharmaceutically acceptable salts include the sulfate salt ethanolate and sulfate salts.

The term "polymorphic form" refers to the property of darunavir to exist in amorphous form, in polymorphic form, in crystalline form with distinct structures varying in crystal hardness, shape and size. The different crystalline forms can be detected by crystallographic techniques or indirectly by assessment of differences in physical and/or chemical properties associated with each particular polymorph. The different polymorphs vary in physical properties such as solubility, dissolution, solid-state stability as well as processing behaviour in terms of powder flow and compaction during tabletting.

The terms "pseudopolymorphic form" or "solvates" refer to aggregates that consists of molecules of darunavir and salts thereof, entrapped or complexed with solvent molecules, on a mol/mol basis and at various degrees of solvation.

The intermediates according to the invention may also exist in their tautomeric forms. Such forms, although not explicitly indicated in the compounds described herein, are intended to be included within the scope of the present invention.

Pure stereoisomeric forms of the compounds and intermediates as mentioned herein are defined as isomers substantially free of other enantiomeric or diastereomeric forms of the same basic molecular structure of said compounds or intermediates. In particular, the term "stereoisomerically pure" concerns compounds or intermediates having a stereoisomeric excess of at least 80% (i. e. minimum 90% of one isomer and maximum 10% of the other possible isomers) up to a stereoisomeric excess of 100% (i. e. 100% of one isomer and none of the other), more in particular, compounds or intermediates having a stereoisomeric excess of 90% up to 100%, even more in particular having a stereoisomeric excess of 94% up to 100% and most in particular having a stereoisomeric excess of 97% up to 100%. The terms "enantiomerically pure" and "diastereomerically pure" should be understood in a similar way, but then having regard to the enantiomeric excess, respectively the diastereomeric excess of the mixture in question.

Pure stereoisomeric forms of the compounds and intermediates of this invention may be obtained by the application of art-known procedures. For instance, enantiomers may be separated from each other by the selective crystallization of their diastereomeric salts with optically active acids or bases. Examples thereof are tartaric acid, dibenzoyltartaric acid, ditoluoyltartaric acid and camphosulfonic acid. Alternatively, enantiomers may be separated by chromatographic techniques using chiral stationary phases. Said pure stereochemically isomeric forms may also be derived from the corresponding pure stereochemically isomeric forms of the appropriate starting materials, provided that the reaction occurs stereospecifically. Preferably, if a specific stereoisomer is desired, said compound will be synthesized by stereospecific processes. These processes will advantageously employ enantiomerically pure starting materials.

The diastereomeric racemates of the compounds and intermediates of this invention can be obtained separately by conventional methods. Appropriate physical separation methods which may advantageously be employed are, for example, selective crystallization and chromatography, e.g. column chromatography.

It is clear to a person skilled in the art that darunavir and intermediates of formulae (3), (4), (5), (6) and (7) contain at least two asymmetric centers and thus may exist as different stereoisomeric forms. These asymmetric centers are indicated with an asterisk (*) in darunavir below. Corresponding centers are present in the above intermediates.

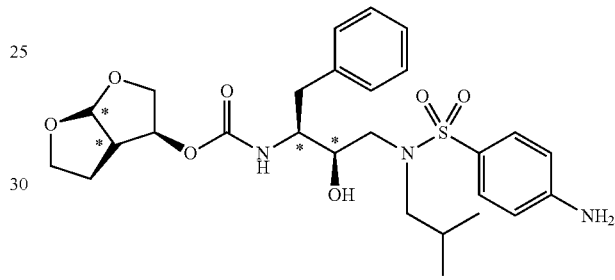

The absolute configuration of each asymmetric center that may be present in darunavir and intermediates of this invention may be indicated by the stereochemical descriptors R and S, this R and S notation corresponding to the rules described in Pure Appl. Chem. 1976, 45, 11-30.

The present invention is also intended to include all isotopes of atoms occurring on the present compounds. Isotopes include those atoms having the same atomic number but different mass numbers. By way of general example and without limitation, isotopes of hydrogen include tritium and deuterium. Isotopes of carbon include C-13 and C-14.

The reagents and solvents used throughout the specification may be replaced by functional alternatives or functional derivatives thereof as they are known to a person skilled in the art. Also the reaction conditions such as stirring times, purification and temperature may be adjusted to optimise reaction conditions. Similarly, the reaction products may be isolated from the medium and, if necessary, further purified according to methodologies generally known in the art such as, for example, extraction, crystallization, trituration and chromatography. A number of intermediates and starting materials used in the foregoing preparations are known compounds, while others may be prepared according to methods known in the art of preparing said or similar compounds.

The present invention also relates to HIV protease inhibitors and any pharmaceutically acceptable salt, polymorphic or pseudopolymorphic form thereof, obtained by using any intermediate as described herein, wherein such compounds and intermediates are prepared as described in the present invention.

The present invention also relates to HIV protease inhibitors such as darunavir and any pharmaceutically acceptable salt, polymorphic or pseudopolymorphic form thereof, obtained by using at least one compound of formula (3'), (4) or (5) as an intermediate.

The present invention also relates to the compound of formula (3') for use in the preparation of a HIV protease inhibitor such as darunavir and any pharmaceutically acceptable salt, polymorphic or pseudopolymorphic form thereof.

The present invention also relates to the compound of formula (4) for use in the preparation of a HIV protease inhibitor such as darunavir and any pharmaceutically acceptable salt, polymorphic or pseudopolymorphic form thereof.

The present invention also relates to the compound of formula (5) for use in the preparation of a HIV protease inhibitor such as darunavir and any pharmaceutically acceptable salt, polymorphic or pseudopolymorphic form thereof.

The present invention also relates to a process for the preparation of a HIV protease inhibitor such as darunavir and any pharmaceutically acceptable salt, polymorphic or pseudopolymorphic form thereof in which a compound of formula (3') is employed.

The present invention also relates to a process for the preparation of a HIV protease inhibitor such as darunavir and any pharmaceutically acceptable salt, polymorphic or pseudopolymorphic form thereof in which a compound of formula (4) is employed.

The present invention also relates to a process for the preparation of a HIV protease inhibitor such as darunavir and any pharmaceutically acceptable salt, polymorphic or pseudopolymorphic form thereof in which a compound of formula (5) is employed.

The following examples are meant to illustrate the present invention. The examples are presented to exemplify the invention and are not to be considered as limiting the scope of the invention.

In the following Examples gas chromatography (GC) and high pressure liquid chromatography (HPLC) analyses were performed using the following systems:

Gas Chromatography:

Column: Agilent HP-1 30m×320 um×0.25 um

Carrier: Nitrogen, 1.1 ml/min

Injector Temperature: 200° C.

Split Ratio 80:1

Detector Temperature: 250° C.

$H_2$: 30 ml/min

Ai: 400 ml/min $N_2$: 30 ml/min

Column Temperature: Start 40° C.

Start Temperature: 4 min

Speed: 10° C./min

End: 200° C.

End Temperature: 5 min

High Pressure Liquid Chromatography:

Column: ZORBAX Eclipse XDB-C18 4.6×250 mm, 5 μm;

Speed: 1.0 mL/min (except where specified);

Column Temperature: 30° C.,

UV: 210 nm (except where specified);

The mobile phase and solvent are specified for each compound.

Examples

1) Preparation of Compound (2)

(2)

a) In a 50 liter glass-lined reactor, 3.5 kg benzaldehyde was dissolved in 7.1 kg methanol and then 3.6 kg isobutylamine was added. The addition speed of isobutylamine was controlled so that the temperature of the mixture was maintained lower than 50° C. The mixture was stirred at 18~36° C. for 2 hours. GC analysis showed that the content of benzaldehyde was less than 0.05% by GC area; retention time of benzaldehyde: 9.982 min. The solvent was removed under reduced pressure (<40° C./0.085 MPa). The residual imine (2') was 98.5% pure by GC area content; retention time: 15.121 min.

(2')

b) To a solution of the residue obtained in stage a) in 15.4 kg of methanol 1.35 kg of sodium borohydride ($NaBH_4$) was added in small portions at 0~5° C. The mixture was stirred for 1.5 hours at 1.5° C.~6.4° C., and then at about 15° C. for one hour. The mixture was concentrated under reduced pressure (<40° C./0.085 MPa) and 12.5 kg of water was added. The aqueous layer was then extracted three times with 22 kg of methyl tertiarybutyl ether (MTBE). The organic phase was washed with 11.4 kg of brine, dried over 1 kg of sodium sulfate, filtered and concentrated. Compound (2) was obtained in the reactor as a yellowish oil, of purity 95.6% by HPLC area, mobile phase: MeCN/15 mmol/L $KH_2PO_4$ 0.1% W/V TEA (50/50); retention time: 5.542 min., and directly used in the next stage of the process.

2) Preparation of Compound (3')

(3')

Compound (2) was dissolved in 8.3 kg isopropyl alcohol and 4 kg of compound (1')

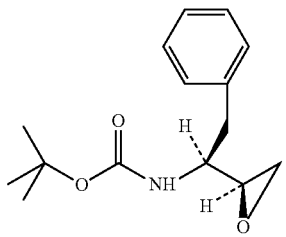
(1')

was added to the solution; then the mixture was heated to 82° C. for 3 hours. The excess of methanol was removed under reduced pressure (<40° C./0.085 MPa). Into the system 4.8 kg of MTBE was added and the mixture stirred at room temperature, then the temperature was lowered to −5.9° C. The product was re-crystallized in MTBE and compound (3') was obtained as an off-white solid, weight 4.6 kg (yield 70.7%, purity 99.6% by HPLC area, mobile phase: MeCN/15 mmol/L $KH_2PO_4$ 0.1% W/V TEA (80/20); retention time: 12.550 min.). The product was analysed with the following results.

Elementary Analysis:
C: theoretical 72.30% found 73.20%. H: theoretical 8.98% found 9.20%. N theoretical 6.57% found 6.57%.

NMR Analysis:
For the analysis the compound was dissolved in deuterated chloroform.

A Bruker AVANCE-400 MHz NMR spectrometer equipped with a Bruker 5 mm CPDUL 1H/2H-13C Z-GRD high resolution probe and running TOPSPIN 2.0 software, was used to collect 1-dimensional proton and carbon.

The 1H and 13C NMR spectra obtained and the following results are consistent with the covalent structure for the product.

1H NMR (600 MHz, CHLOROFORM-d) δ ppm 0.86 (d, J=6.80 Hz, 3H) 0.89 (d, J=6.80 Hz, 3H) 1.34 (s, 9H) 1.51 (br. s., 1H) 1.77-1.85 (m, 1H) 2.18-2.25 (m, 2H) 2.44 (dd, J=12.84, 3.40 Hz, 1H) 2.52 (dd, J=12.46, 10.20 Hz, 1H) 2.78 (br. s., 1H) 2.87 (dd, J=13.97, 3.79 Hz, 1H) 3.36 (d, J=13.60 Hz, 1H) 3.58 (br. s., 1H) 3.72 (br. s., 1H) 3.76 (d, J=13.60 Hz, 1H) 4.49 (br. s., 1H) 7.15 (d, J=7.18 Hz, 2H) 7.17 (t, J=7.18 Hz, 1H) 7.22-7.27 (m, 5H) 7.31 (t, J=7.55 Hz, 2H)

13C NMR (151 MHz, CHLOROFORM-d) δ ppm 20.63 (s, 1C) 20.93 (s, 1C) 26.27 (s, 1C) 28.33 (s, 3C) 36.13 (br. s., 1C) 54.50 (br. s., 1C) 58.13 (s, 1C) 59.48 (s, 1C) 63.18 (s, 1C) 69.10 (br. s., 1C) 79.20 (br. s., 1C) 126.18 (s, 1C) 127.23 (s, 1C) 128.27 (s, 2C) 128.39 (s, 2C) 129.19 (s, 2C) 129.62 (s, 2C) 138.17 (s, 1C) 138.67 (s, 1C) 155.49 (br. s., 1C).

MS Analysis:
High-resolution mass spectrometric analysis was performed on a Q-T of-2 instrument using high performance liquid chromatography electrospray ionization mass spectrometry (HPLC-ESI-MS). The molecular weight of the product was established by HPLC-ESI-MS and was further supported by exact mass measurements. The molecular weight was evident from the ESI mass spectrum that displays an intense signal at m/z 427.3 $(M+H)^+$. The difference between the exact mass measurement (427.2961) and calculated mass is 0.1 ppm.

MS (ESI) m/z 427.3 $(M+H)^+$

MS/MS (ESI) m/z 427.3 $(M+H)^+$, m/z 371.2 (loss of tertiary butyl), m/z 327.2 (loss of BOC), m/z 292.2, m/z 254.1, m/z 208.1, m/z 176.1, m/z 164.1, m/z 91.1.

3) Preparation of 1-([[(3R,3aS,6aR)hexahydrofuro[2,3-b]furan-3-yloxy]carbonyl]-oxy)-2,5-pyrrolidinedione

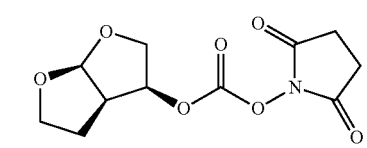 [SMILES: O=C(O[C@@H]1CO[C@@H]2OCC[C@@H]21)ON1C(=O)CCC1=O]

In a glass-lined reactor 17.7 kg (3R,3aS,6aR)-hexahydrofuro[2,3-b]furan-3-ol in acetonitrile (30%) was added, then 3.9 kg of triethylamine 9 kg of solid disuccinimidyl carbonate (DSC) was added in portions, while keeping the reaction temperature below 35° C. The reaction mixture was stirred at 20° C. for 3 hours. The temperature was lowered to 2° C. and 45 kg of ice-water was added to the reactor. Precipitation was observed and the precipitate was filtered off. The cake was dissolved in 41 kg of chloroform and the aqueous phase was separated. The solution was evaporated to dryness and 18.8 kg of petroleum ether was added to the reactor containing the residue. The mixture was stirred at 0-5° C. for 1 hour. The resulting white precipitation was filtered off and rinsed with about 2 kg of petroleum ether. 1-([[(3R,3aS,6aR)hexahydrofuro[2,3-b]furan-3-yloxy]carbonyl]oxy)-2,5-pyrrolidinedione was obtained as an off-white solid, weight 3.69 kg (yield 39.9%, purity 68.7% by HPLC area, mobile phase: $CH_3CN$/15 mmol/L $Na_2HPO_4$, pH 3.0 by $H_3PO_4$ (35/65); speed: 0.8 mL/min; retention time: 7.730 min.).

4) Preparation of Compound (4)

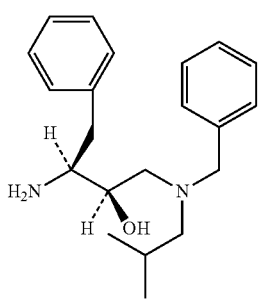
(4)

4.6 kg of compound (3') was dissolved in 20 kg ethanol and 2.8 kg of 36% hydrochloric acid was added. The solution was then heated at 78° C. for 4 hours, then cooled down to 40° C. Toluene (10 kg) was added and the solvents were removed under reduced pressure (<40° C./0.085 MPa). Compound (4) was obtained as a white solid (purity 98.6% by HPLC area, mobile phase: MeCN/15 mmol/L $KH_2PO_4$/0.1% W/V TEA (80/20); retention time: 6.106 min) and retained in the reactor for the next stage of the process.

5) Preparation of Compound (5)

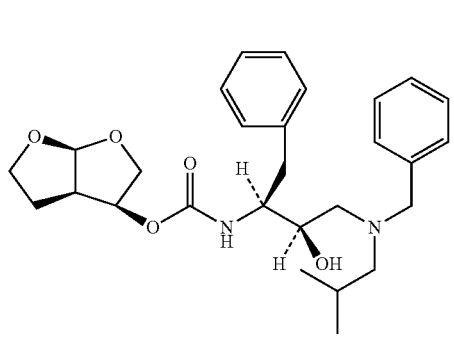
(5)

Compound (4) retained in the reactor from the previous stage was dissolved in 20.4 kg of dimethylformamide, 3.9 kg triethylamine was added to provide a pH of 7~8, then 3.3 kg of 1-([[(3R,3aS,6aR)hexahydrofuro[2,3-b]furan-3-yloxy]carbonyl]oxy)-2,5-pyrrolidinedione was added to the mixture which was then stirred at 15° C.~18° C. for about 5 hours. Water was slowly added and precipitation was observed. The precipitate was filtered off and the cake was dissolved in 71 kg of chloroform. The aqueous phase was separated off. Chloroform was removed from the organic phase under reduced pressure (<30° C./0.085 MPa). Compound (5) was obtained as a white glassy solid (purity: 96.4% by HPLC area, mobile phase: MeCN/15 mmol/L $KH_2PO_4$/0.1% W/V TEA (60/40); retention time: 18.322 min.) and retained in the reactor for the next stage of the process.

6) Preparation of Compound (6)

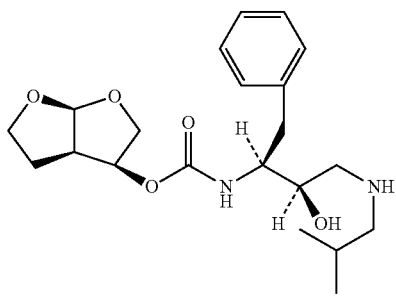
(6)

Compound (5) retained in the reactor from the previous stage was dissolved in 26 kg of methanol. Wet (68% water) 10% Pd/C, 1.36 kg, was washed with ethanol and added to the solution. The mixture was stirred for about 5.5 hours at about 21° C.~46° C. under 0.5 Mpa of hydrogen. The mixture was filtered and the filtrate concentrated at 40° C. 8 kg of ethanol and 17 kg of petroleum ether were added to the residue, crystallization occurred and compound (6) was obtained as an off-white crystalline product, weight 3.2 kg (yield 73.34%, purity 96.7% by HPLC area, mobile phase: MeCN/15 mmol/L $KH_2PO_4$/0.1% TEA (W/V=60/40); retention time: 2.746 min.).

7) Preparation of Compound (7)

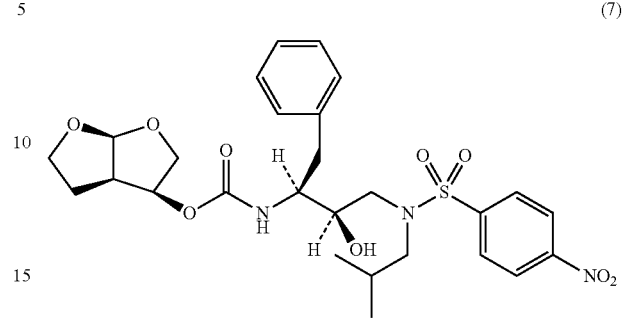
(7)

3.2 kg of compound (6) obtained in the previous stage was dissolved in 52 kg of chloroform and 3.0 kg of triethylamine was added to the solution. 1.9 kg of p-nitrobenzene sulfonyl chloride was added to the mixture portion-wise at 0-5° C., then stirred at 20° C. for 4 hours. The organic solution was washed twice with 46.8 kg of saturated sodium hydrogen carbonate solution and three times with 42 kg of 5% aqueous sodium chloride solution and dried over magnesium sulfate, and then decolored with 0.07 kg active carbon. The filtrate was concentrated at 65° C. The crude product was re-crystallized in 10 kg of ethyl acetate and 17 kg of petroleum ether. Compound (7) was obtained as an off-white solid, weight 4.12 kg (yield 84.6%, purity 96.3% by HPLC area, solvent: MeCN/Water (50/50), mobile phase: MeCN/Water (45/55), UV: 215 nm; retention time: 16.424 min.).

8) Preparation of Darunavir

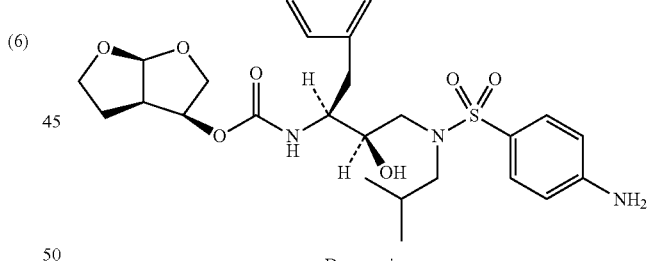

Darunavir 4.12 kg of compound (7) was dissolved in 30 kg of ethyl acetate. 1.35 kg of wet (68% water) 10% Pd/C was washed with ethyl acetate and added to the solution. The mixture was stirred at 25.6° C.~57° C. for about 0.6 h under 0.5 Mpa of hydrogen. To the mixture was added 0.31 kg of active carbon, the mixture was filtered and the filtrate concentrated under reduced pressure (<25° C./0.085 MPa). The residue was re-crystallized with 15 kg of ethanol. Darunavir (as the ethanolate) was obtained as an off-white solid, weight 2.9 kg (yield 73.6%, purity 99.2% by HPLC area, solvent: MeCN/Water (50/50), mobile phase MeCN/Water (45/55), UV: 215 nm; retention time: 9.072 min.). The final product was analysed by IR spectroscopy and determined to have an IR spectrum corresponding to a reference spectrum of an authentic sample of the product.

The invention claimed is:

1. A process for the preparation of darunavir of formula (A) or the ethanolate solvate thereof:

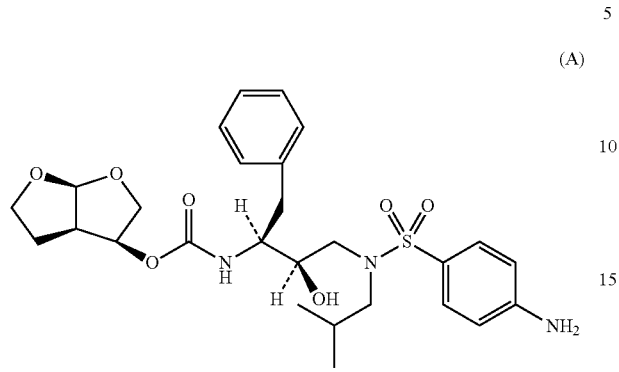

(A)

which comprises:

(i) reacting a compound of formula (1):

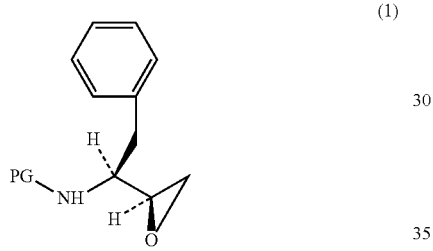

(1)

wherein PG represents an amino protecting group, with N-benzyl-isobutylamine, namely a compound of formula (2):

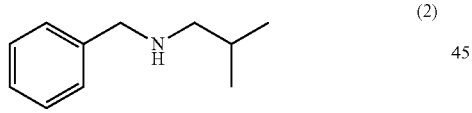

(2)

to obtain a compound of formula (3):

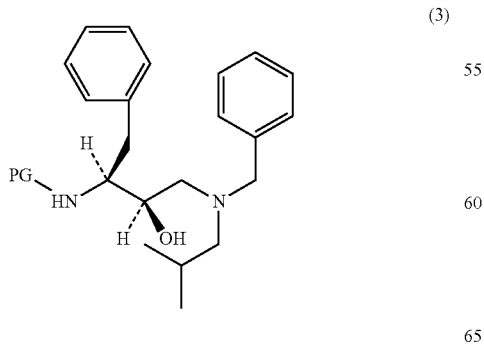

(3)

(ii) treating the compound of formula (3) to remove the PG protecting group to obtain a compound of formula (4):

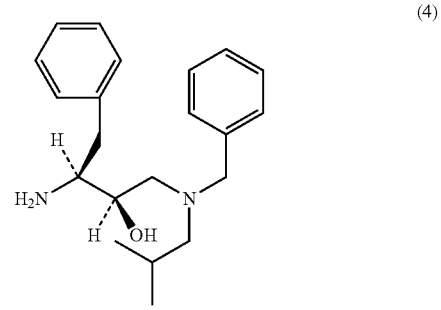 [SMILES: CC(C)CN(Cc1ccccc1)C[C@@H](O)[C@@H](N)Cc1ccccc1]

(4)

(iii) coupling the compound of formula (4) with 1-([[(3R, 3aS,6aR)hexahydrofuro[2,3-b]furan-3-yloxy]-carbonyl]oxy)-2,5-pyrrolidinedione of formula:

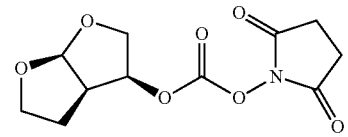 [SMILES: O=C(O[C@@H]1CO[C@@H]2OCC[C@@H]21)ON1C(=O)CCC1=O]

to obtain compound of formula (5):

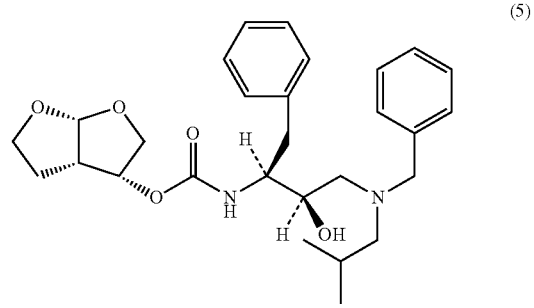 [SMILES: CC(C)CN(Cc1ccccc1)C[C@@H](O)[C@H](Cc1ccccc1)NC(=O)O[C@H]1CO[C@H]2OCC[C@H]21]

(5)

(iv) removing the N-benzyl group from the compound of formula (5) to obtain a compound of formula (6):

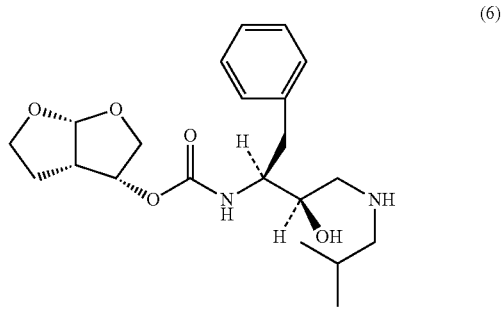 [SMILES: CC(C)CNC[C@@H](O)[C@H](Cc1ccccc1)NC(=O)O[C@H]1CO[C@H]2OCC[C@H]21]

(6)

(v) introducing a p-nitrophenylsulfonyl group into the compound of formula (6) to obtain a compound of formula (7):

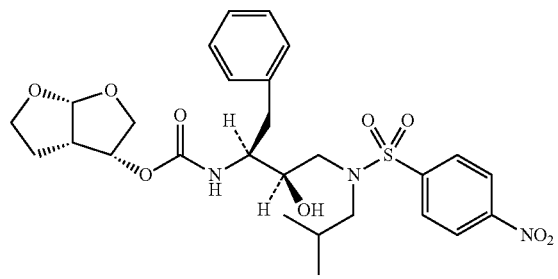

(7)

(vi) reducing the nitro group of the compound of formula (7) to form darunavir (vii) and thereafter recrystallizing from ethanol if the ethanolate solvate is desired.

2. A process according to claim 1 in which a compound of formula (1') is reacted with N-benzyl-isobutylamine of formula (2) to yield a compound of formula (3'):

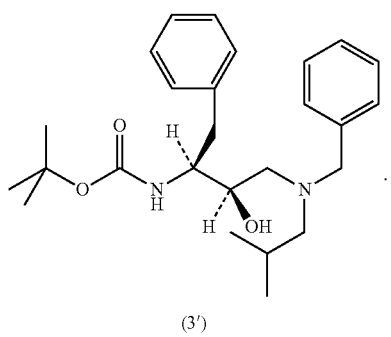

(1')

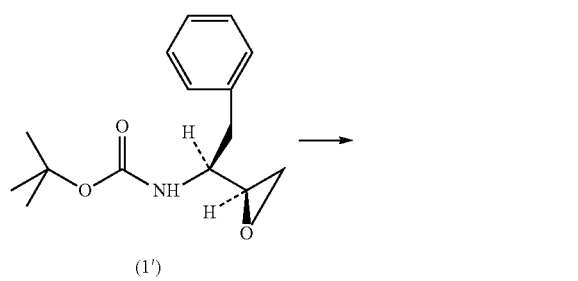

(3')

3. A process according to claim 1 in which the compound of formula (3) is treated by acid hydrolysis to remove the protecting group.

4. A process according to claim 1 for the preparation of a compound of formula (5) which comprises coupling the compound of formula (4) with 1-([[(3R,3aS,6aR)hexahydrofuro[2,3-b]furan-3-yloxy]carbonyl]oxy)-2,5-pyrrolidinedione of formula:

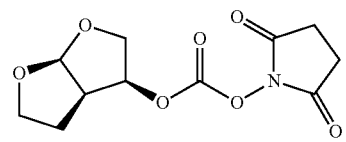 [SMILES: O=C(O[C@@H]1CO[C@@H]2OCC[C@@H]21)ON1C(=O)CCC1=O]

to obtain a compound of formula (5):

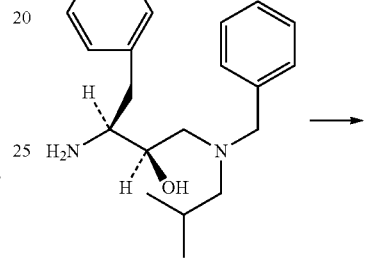

(4)

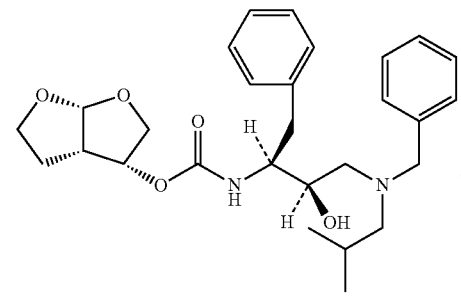

(5)

5. A process according to claim 1 in which removal of the N-benzyl group is effected by catalytic reduction of the compound of formula (5).

6. A compound of formula (3'):

(3')

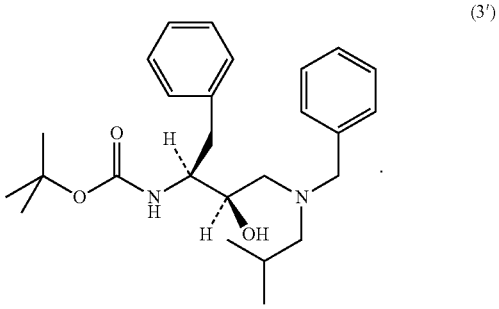 [SMILES: CC(C)CN(Cc1ccccc1)C[C@@H](O)[C@H](Cc1ccccc1)NC(=O)OC(C)(C)C]

7. A compound of formula (4):
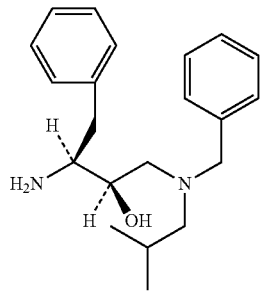
(4)
8. A compound of formula (5):
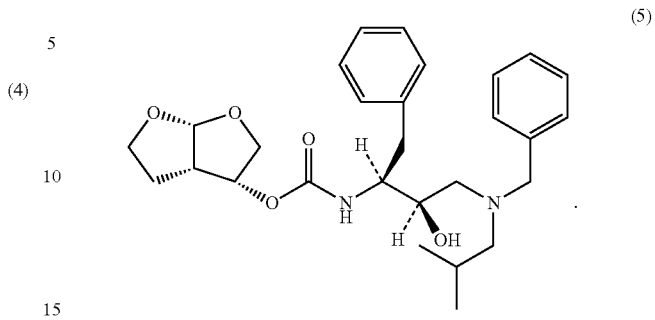
(5)
9. A process according to claim 2 in which the compound of formula (3') is treated by acid hydrolysis to remove the protecting group.
* * * * *

UNITED STATES PATENT AND TRADEMARK OFFICE
CERTIFICATE OF CORRECTION

| | | |
|---|---|---|
| PATENT NO. | : 8,580,981 B2 | Page 1 of 1 |
| APPLICATION NO. | : 13/060942 | |
| DATED | : November 12, 2013 | |
| INVENTOR(S) | : Wigerinck et al. | |

It is certified that error appears in the above-identified patent and that said Letters Patent is hereby corrected as shown below:

In the Claims:

Claim 9, in column 32, line 16, change "2" to "3"

Signed and Sealed this
Twenty-second Day of July, 2014

Michelle K. Lee
*Deputy Director of the United States Patent and Trademark Office*